(12) United States Patent
Ho et al.

(10) Patent No.: US 12,186,351 B2
(45) Date of Patent: Jan. 7, 2025

(54) COMPOSITION FOR MODULATING IMMUNITY AND THE USE THEREOF

(71) Applicant: Lytone Enterprise, Inc., New Taipei (TW)

(72) Inventors: Chia-Shin Ho, New Taipei (TW); Wei-Ting Chang, New Taipei (TW); Wei-Ting Tseng, New Taipei (TW); Tien-Hung Chang, New Taipei (TW)

(73) Assignee: LYTONE ENTERPRISE, INC., New Taipei (TW)

( * ) Notice: Subject to any disclaimer, the term of this patent is extended or adjusted under 35 U.S.C. 154(b) by 0 days.

(21) Appl. No.: 17/548,806

(22) Filed: Dec. 13, 2021

(65) Prior Publication Data
US 2022/0184152 A1 Jun. 16, 2022

Related U.S. Application Data

(60) Provisional application No. 63/124,295, filed on Dec. 11, 2020.

(51) Int. Cl.
| | | |
|---|---|---|
| A61K 35/747 | (2015.01) |
| A61K 31/716 | (2006.01) |
| A61K 35/20 | (2006.01) |
| A61P 37/02 | (2006.01) |

(52) U.S. Cl.
CPC .......... *A61K 35/747* (2013.01); *A61K 31/716* (2013.01); *A61K 35/20* (2013.01); *A61P 37/02* (2018.01)

(58) Field of Classification Search
CPC .... A61K 35/747; A61K 31/716; A61K 35/20; A61K 35/74; A61K 2300/00; A61P 37/02; A61P 37/00
See application file for complete search history.

(56) References Cited

U.S. PATENT DOCUMENTS

| | | | |
|---|---|---|---|
| 8,372,392 B2 * | 2/2013 | Chang ................ | A61P 11/02 435/252.9 |
| 2021/0000886 A1 * | 1/2021 | Zrust ................ | C12Q 1/686 |

FOREIGN PATENT DOCUMENTS

| | | |
|---|---|---|
| CN | 102168043 B | 4/2013 |
| CN | 105454924 A | 4/2016 |
| CN | 105454966 A | 4/2016 |
| CN | 108065400 A | 5/2018 |
| CN | 109221864 A | 1/2019 |

(Continued)

OTHER PUBLICATIONS

McGee, D. W., et al. "A synergistic relationship between TNF-alpha, IL-1 beta, and TGF-beta 1 on IL-6 secretion by the IEC-6 intestinal epithelial cell line." Immunology 86.1 (1995): 6. (Year: 1995).*

(Continued)

*Primary Examiner* — Louise W Humphrey
*Assistant Examiner* — Candice Lee Swift
(74) *Attorney, Agent, or Firm* — Birch, Stewart, Kolasch & Birch, LLP

(57) ABSTRACT

Disclosed herein is a composition for modulating immunity, comprising *Lactobacillus paracasei* LT12, β-glucan, and Bovine Colostrum Powder. Also provided is a method for modulating immunity, comprising administering to a subject in need a therapeutically effective amount of the composition, wherein the method is to enhance the expression of IL-6, IL-10, TNF-α and TGF-β1.

14 Claims, 2 Drawing Sheets

(56) References Cited

FOREIGN PATENT DOCUMENTS

| | | | |
|---|---|---|---|
| CN | 110150384 A | 8/2019 | |
| CN | 112913925 A | 6/2021 | |
| CN | 113519624 A | 10/2021 | |
| EP | 2 338 977 A1 | 6/2011 | |

OTHER PUBLICATIONS

Estrada, Alberto, et al. "Immunomodulatory activities of oat β-glucan in vitro and in vivo." Microbiology and immunology 41.12 (1997): 991-998. (Year: 1997).*

Hagiwara, Katsuro, et al. "Detection of cytokines in bovine colostrum." Veterinary immunology and immunopathology 76.3-4 (2000): 183-190. (Year: 2000).*

Arena, Mattia Pia, et al. "Combinations of cereal β-glucans and probiotics can enhance the anti-inflammatory activity on host cells by a synergistic effect." Journal of functional foods 23 (2016): 12-23. (Year: 2016).*

ORFFA Pet Food Supplement, Jul. 2020, https://orffa.com/publications/beta-1-3-1-6-glucans-balance-immunity-using-nutrition/; accessed Dec. 8, 2022 (Year: 2020).*

Noble, P. W., et al. "Transforming growth factor-beta primes macrophages to express inflammatory gene products in response to particulate stimuli by an autocrine/paracrine mechanism." Journal of immunology (Baltimore, Md.: 1950) 151.2 (1993): 979-989. (Year: 1993).*

Russo, Pasquale, et al. "Beta-glucans improve growth, viability and colonization of probiotic microorganisms." International journal of molecular sciences 13.5 (2012): 6026-6039. (Year: 2012).*

Extended European Search Report issued May 4, 2022, in European Patent Application No. 21213984.4.

Office Action and Search Report issued Oct. 25, 2023, in Taiwan Patent Application No. 110146636.

Wei et al., "Synergistic effects of Lactobacillus rhamnosus ZDY114 and bovine colostrums on the immunological function of mouse in vivo and in vitro," Appl. Microbiol. Biotechnol. (2007), vol. 75, No. 2, pp. 427-434.

\* cited by examiner

COMPOSITION FOR MODULATING IMMUNITY AND THE USE THEREOF

CROSS REFERENCE TO RELATED APPLICATIONS

This application claims priority to U.S. Provisional Application No. 63/124,295 filed on Dec. 11, 2020, the entire contents of which are hereby incorporated by reference.

FIELD OF THE INVENTION

The present invention relates to a composition or a method for modulating immunity.

BACKGROUND OF THE INVENTION

For the infection pattern of most influenza viruses or pathogenic bacteria, the pathogens infect and colonize a host when the host has a weakened immune system. In order to eliminate the pathogens after the infection, the host may have cytokine storm, which is an immune overreaction that causes inflammation and leads to organ and tissue damage (such as pneumonia) when the immune system is overloaded. Therefore, an immune system that is too strong or too weak may cause diseases. It is important to have a well-balanced immune system, so that the immune system can be boosted to fight against foreign objects such as microorganisms and viruses during the infection, and the immune system can be reduced to alleviate inflammation during cytokine storm caused by sensitizing factors. Such two-way immunomodulation can make the immune system balanced and maintain good health.

In the early stage, innate immunity is mainly the first line of defense against invading pathogens in the human immune system. The innate immune responses, which are a rapid anti-infective action, non-specifically identify and act on pathogens, directly fight against pathogens to resist external infections. The sentinel innate immune cells are responsible for activating the innate and adaptive immunity to pathogens. Macrophages are a key indicator of host defense through pathogen phagocytosis. Activation through different signaling pathways results in two types of macrophages with different functions: pro-inflammatory (classically activated macrophage, M1) and anti-inflammatory (alternatively activated macrophage, M2). Polarized M1 and M2 macrophages can be reversibly functionally redifferentiated into pro-inflammatory and anti-inflammatory macrophages, respectively. The role of M1 macrophages is to secrete pro-inflammatory cytokines and chemokines, mainly IL-6, IL-12 and TNF-α, present antigens, and thus participate in the immune response and help drive antigen-specific Th1 cell inflammatory reaction. In addition, the polarization of the M1 phenotype is considered to be essential for an effective antiviral immune response in the lungs. M2 macrophages mainly secrete Arginase-I, IL-10 and TGF-β and other anti-inflammatory cytokines, which have the function of reducing inflammation, and contributing to tumor growth and immunosuppressive function. In short, M1 and M2 macrophages can transform into each other in a specific microenvironment.

To maintain good health, how to prevent a weakened immune system that causes virus infection is the first line of defense that should be strictly guarded. Nowadays, dietary supplements are one of the common methods to prevent the occurrence of infectious disease and allergies. However, most dietary supplements are focus on one-way immunomodulation, either enhancing immunity or reducing allergies.

Accordingly, it is desirable to develop a product with two-way immunomodulatory effects.

SUMMARY OF THE INVENTION

It is unexpectedly found in the present invention that the combination of the three functional ingredients, LT12, BG and BCP, can efficiently induce the production of TNF-α, IL-6, and TGF-β1, suggesting the synergistic or additive effects among the three ingredients. Accordingly, the present invention provides a composition for modulating immunity which provides multi-functional synergistic effects, and the use thereof.

Accordingly, one aspect of the present invention is to provide a composition for modulating immunity, comprising *Lactobacillus paracasei* LT12 (LT12), β-glucan (BG), and Bovine Colostrum Powder (BCP) at a ratio to provide multi-functional synergistic effects for modulating immunity, particularly in enhancing the expression of tumor necrosis factor alpha (TNF-α), interleukin-6 (IL-6), interleukin-10 (IL-10) and transforming growth factor-β1 (TGF-β1).

In one embodiment of the present invention, the composition consists essentially of 0.5%-20% of *Lactobacillus paracasei* strain LT12 (LT12), 0.5%-25% of β-glucan (Beta-Glucan, BG) and 0.05%-10% of Bovine Colostrum powder (BCP) as active components, in a percentage by total weight of the composition.

In a particular embodiment of the present invention, the composition consists essentially of 1%-10% of *Lactobacillus paracasei* strain LT12 (LT12), 1%-12% of β-glucan (Beta-Glucan, BG) and 0.05%-5% of Bovine Colostrum powder (BCP) as active components, in a percentage by total weight of the composition.

In a particular embodiment of the present invention, the composition the composition consists essentially of 1%-5% of *Lactobacillus paracasei* strain LT12 (LT12), 1%-6% of β-glucan (Beta-Glucan, BG) and 1%-4% of Bovine Colostrum powder (BCP) as active components, in a percentage by total weight of the composition.

In a particular embodiment of the present invention, the composition the composition consists essentially of 2%-4% of *Lactobacillus paracasei* strain LT12 (LT12), 4%-5% of β-glucan (Beta-Glucan, BG) and 1%-2% of Bovine Colostrum powder (BCP) as active components, in a percentage by total weight of the composition.

In one embodiment of the invention, the β-glucan is yeast β-1,3/1,6-glucan.

In one embodiment of the invention, the composition further comprises a pharmaceutically acceptable or edible carrier.

In another aspect, the present invention provides a pharmaceutical composition for modulating immunity, comprising a pharmaceutically acceptable carrier, and *Lactobacillus paracasei* strain LT12 (LT12), β-glucan (BG), and Bovine Colostrum powder (BCP) at a ratio to provide synergistic effects in enhancing expression of tumor necrosis factor alpha (TNF-α), interleukin-6 (IL-6), interleukin-10 (IL-10) and/or transforming growth factor-β1 (TGF-β1).

In a further aspect, the present invention provides a dietary supplement for modulating immunity, comprising a dietary acceptable carrier, and *Lactobacillus paracasei* strain LT12 (LT12), β-glucan (BG), and Bovine Colostrum powder (BCP) at a ratio to provide synergistic effects in enhancing expression of tumor necrosis factor alpha (TNF-α), interleukin-6 (IL-6), interleukin-10 (IL-10) and/or transforming growth factor-β1 (TGF-β1).

In a yet aspect, the present invention provides a method for modulating immunity, comprising administering to a subject in need a therapeutically effective amount of the composition according to the invention.

In a further yet aspect, the present invention provides a use of a composition in the manufacturing of a medicament or a dietary supplement of modulating immunity, wherein the composition comprises *Lactobacillus paracasei* LT12, β-glucan, and Bovine Colostrum Powder.

According to the present invention, the composition does not affect the viability of macrophage.

It is to be understood that both the foregoing general description and the following detailed description are exemplary and explanatory only and are not restrictive of the invention.

BRIEF DESCRIPTION OF THE DRAWINGS

FIG. 3A shows the effects of the samples on the secretion of TNF-α. FIG. 3B shows the effects of the samples on the secretion of IL-6. FIG. 3C shows the effects of the samples on the secretion of TGF-β1. FIG. 3D shows the effects of the samples on the secretion of IL-10.

DETAILED DESCRIPTION OF THE INVENTION

Figure 1:
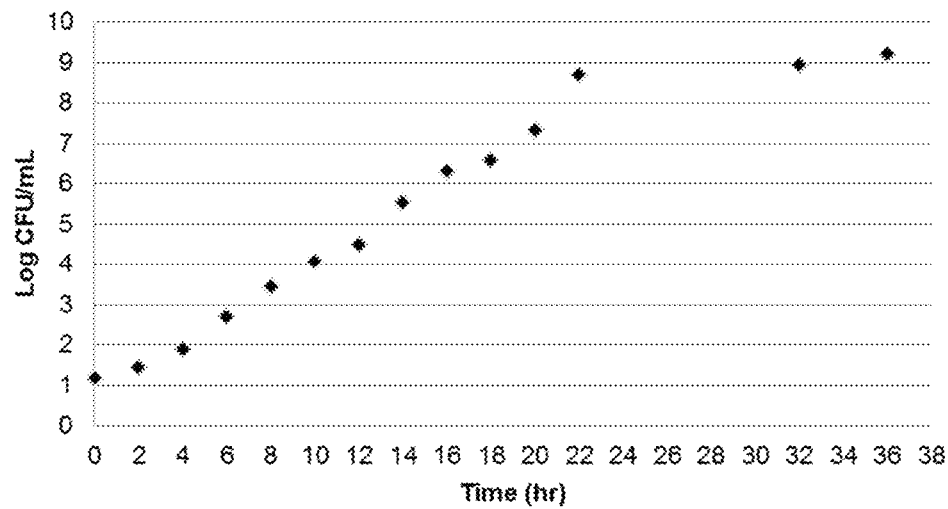
FIG. 1 shows the growth status of *Lactobacillus paracasei* LT12 in MRS medium.

Unless defined otherwise, all technical and scientific terms used herein have the same meaning as commonly understood by a person skilled in the art to which this invention belongs.

As used herein, the term "a" or "an" means one or more than one (that is, at least one) of the grammatical object of the article, unless otherwise made clear in the specific use of the article in only a singular sense.

The present invention provides a composition for modulating immunity, comprising three single ingredients: *Lactobacillus paracasei* LT12 (LT12), β-glucan (BG) and Bovine Colostrum Powder (BCP), and the use thereof.

*Lactobacillus* species constitute a significant component of the human and animal microbiota at a number of body sites, such as the digestive system, and the female genital system. Among *Lactobacillus* species, a new strain of *Lactobacillus paracasei*, LT12 (hereinafter LT12), was developed and has been granted patents in many countries, e.g., U.S. Pat. No. 8,372,392 and European Patent No. 2,338,977. The studies showed that LT12 could stimulate human peripheral blood mononuclear cells (PBMCs) to secrete a large amount of IFN-γ and effectively inhibited allergic reactions as well. The results of the cytokine antibody array analysis showed that LT12 could simultaneously enhance the expression of multiple cytokines, including IL-1, IL-6, IL-10, MCP-2 and TNF-α, indicating that LT12 has effects of coordinating immune system and two-way immunomodulation. In accordance with the Budapest Treaty, the strain LT12 used in this disclosure was deposited with the American Agricultural Research Culture Collection, International Depositary Authority, 1815 N. University Street, Peoria, Ill., 61601, USA, on Sep. 21, 2009, with its deposit number NRRL-B50327 for U.S. Pat. No. 8,372,392.

As used herein, the term "β-Glucans" or "BG" refers to a group of β-D-glucose polysaccharides typically forming a linear backbone with 1-3 β-glycosidic bonds. β-glucan molecules can also have branching glucose side-chains attached to other positions on the main D-glucose chain, for example, β-1,3/1,6-glucan having 1-6 side-chains. In the present invention, the β-glucans can be derived from any resources available, for example, β-glucans naturally occurring in the cell walls of cereals, bacteria, and fungi. One example of the β-glucans is β-1,3/1,6-glucan. In one example of the invention, the beta-glucan made from yeast: for example, yeast β-glucan or yeast β-1,3/1,6-glucan.

Colostrum is the first milk produced post-partum by mammals and is compositionally distinct from mature milk. The term "Bovine Colostrum Powder" as used herein is the dried powder of bovine colostrum, wherein the bovine colostrum is the first form of milk produced by the mammary glands of a cow immediately following delivery of the newborn calves.

The term "composition" as used herein, refers a product that results from the mixing or combining of more than one active ingredient. It can be prepared by mixing multiple active ingredients with a pharmaceutically acceptable or edible carrier, which can be prepared according to any commonly used or standard methods in the art.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition as disclosed herein required to provide a clinically significant effect on modulating immunity. An appropriate "effective" amount in any individual case may be determined using known techniques, such as a dose escalation study.

One aspect of the present invention is to provide a composition for modulating immunity, comprising *Lactobacillus paracasei* LT12, β-glucan, and Bovine Colostrum Powder. According to the examples, it was confirmed that the composition of the invention enhanced the expression of IL-6, IL-10, TNF-α, and TGF-β1, but did not affect the viability of macrophage.

To conduct the efficacy experiments, one example of the composition of the invention was prepared, consisting essentially of about 3.13% of LT12, about 4% of BG and about 1.5% BCP as active components, in a percentage of total weight of the composition.

In the invention, the immunomodulatory effect of the composition is evaluated by the following methods. MTT assay (3-(4,5-Dimethylthiazol-2-yl)-2,5-diphenyltetrazolium bromide) was used to determine the cell survival rate and analyze the safety and effective concentration of the composition to the cells. Enzyme-linked immunosorbent assay (ELISA) was used to analyze the immunomodulatory effects of the composition, including TNF-α and IL-6 (pro-inflammatory cytokines) related to inflammation and TGF-β1 and IL-10 (anti-inflammatory cytokines) related to anti-inflammatory.

In present invention, it is unexpectedly found that the composition can induce the secretion of IL-6 cytokine in a large amount, and the concentration of the cytokine also increases with time, in a proportional relationship. Also, compared with the control (no stimulation), the composition increases the induction amount by about 25~75 times in 8~24 hours; compared with groups of single ingredient and combinations of two ingredients, the composition increases the induction amount by about 4~40 times, indicating the significantly synergistic effects of the composition. In addition, compared with other groups, the composition can increase the secretion of TNF-α by about 1~10 times, which also indicates the synergistic effects of the composition. Furthermore, in the analysis of the anti-inflammatory cytokine, TGF-1, compared with the control (no stimulation), the composition increases the induction amount by about 20~30 times in a short period of time (2~4 hours); compared with BG, BCP, and groups of combinations of two ingredients, the composition increases the induction amount by about 1~20 times, indicating the significantly synergistic effects of the composition.

In the present invention, the composition consists essentially of LT12, BG and BCP as active components, which synergistically induces and modulates immunity. The composition of the invention has an extremely significantly synergistic effect on inducing IL-6 secretion, and simultaneously induce Th1 and Th2 related cytokines, indicating that the formula has the best two-way immunomodulatory effects among all the test groups, including the groups containing single component or the combinations of two components. Considering the possible pathogenic mechanism of virus, the composition of the present invention was also confirmed to enhance immune effects. The present invention is a comprehensive product for immunomodulation promotion with anti-allergic and immune strengthening activities, which is suitable as a daily dietary supplement to prevent the infection of any pathogen.

The present invention is further illustrated by the following examples, which are provided for the purpose of demonstration rather than limitation.

EXAMPLES

Example 1: The Growth Status of *Lactobacillus paracasei* LT12

The growth curve of LT12 is shown in both Table 1 and FIG. 1. Activated *Lactobacillus paracasei* LT12 was diluted to $10^1$ CFU/mL for cultivation. For the first four hours, the growth of the bacteria was in the lag phase, and from 6 hours after the initiation of cultivation, the bacteria numbers increased one log CFU/mL about every two hours (log phase). The growth of the bacteria entered the stationary phase at 22 hours and has not reached the death phase at 36 hours. The results indicate that the bacteria in this time period (stationary phase) can be used for subsequent experiments. Based on the growth curve, bacteria culture for 8 hours (3.46±0.01 log CFU/mL), 14 hours (5.56±0.12 log CFU/mL), 20 hours (7.34±0.08 log CFU/mL), 22 hours (8.65±0.06 log CFU/mL), and 36 hours (9.15±0.09 log CFU/mL) were collected for the subsequent experiments, which need $10^3$, $10^5$, $10^7$, $10^8$, and $10^9$ CFU/mL bacteria for the experiment design.

TABLE 1

The growth status of *Lactobacillus paracasei* LT12 in MRS medium.

| Cultivation Time (hour) | Numbers of Bacteria (Log CFU/mL) |
| --- | --- |
| 0 | 1.19 ± 0.02 |
| 2 | 1.46 ± 0.02 |
| 4 | 1.9 ± 0.05 |
| 6 | 2.69 ± 0.04 |
| 8 | 3.46 ± 0.01 |
| 10 | 4.09 ± 0.03 |
| 12 | 4.49 ± 0.03 |
| 14 | 5.56 ± 0.12 |
| 16 | 6.32 ± 0.03 |
| 18 | 6.59 ± 0.02 |
| 20 | 7.34 ± 0.08 |
| 22 | 8.65 ± 0.06 |
| 32 | 8.9 ± 0.05 |
| 36 | 9.15 ± 0.09 |

Note:
$5 \times 10^3 = 3.70$ Log CFU/mL; $5 \times 10^5 = 5.70$ Log CFU/mL; $5 \times 10^7 = 7.70$ Log/CFU/mL

Figure 2:
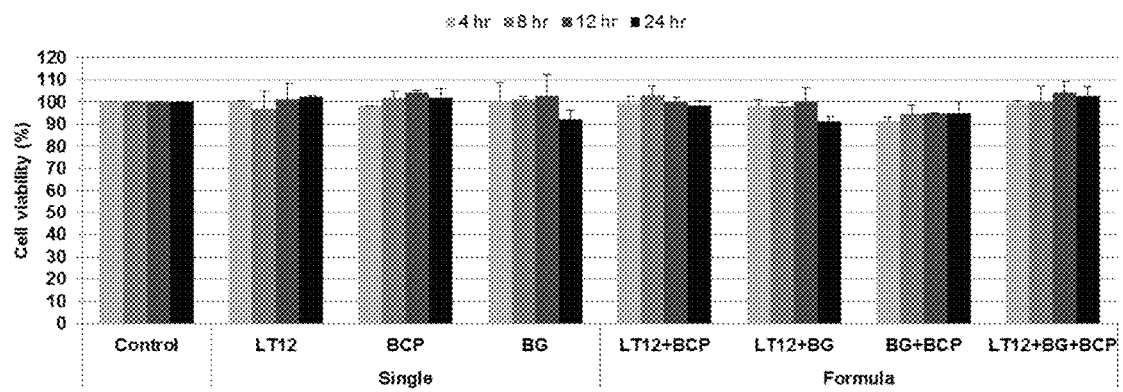
FIG. 2 shows the effects of single ingredients and compound formulae of the samples on the survival rate of macrophage RAW 264.7 cells.

Example 2: The Toxicity Test of Single Ingredients and Compound Formulae of the Samples on the Survival Rate of Macrophage RAW 264.7 Cells First of all, it was confirmed that the samples at the certain concentrations did not have a toxic effect on macrophage RAW264.7. Based on the results of the cytotoxicity test, it was found that both BCP and LT12 could stimulate the proliferation of macrophages RAW264.7, while BG made the cells proliferate within 4 to 12 hours, but slightly reduced the cell viability at 24 hours. In addition, the formula of the present invention did not show cytotoxicity to macrophages RAW264.7. Generally speaking, neither single ingredients nor compound combinations show toxic effect, and the survival rates of macrophages RAW264.7 in all of the groups are more than 90%. These single components and compound combinations do not cause macrophage damage, and some of them can even slightly promote the proliferation of macrophage (FIG. 2).

Example 3: The Immunomodulatory Effects of Single Components and Compound Formulae of the Samples on Macrophage RAW 264.7

After confirming that the formula does not have toxic effect on macrophages RAW264.7, content of cytokines was determined by ELISA. The pro-inflammatory factors (TNF-α, IL-6) and anti-inflammatory factors (TGF-β1, IL-10) that play important roles in the initial stage of the immune response were determined. The results are as shown in FIGS. 3A-3D.

Figure 3A:
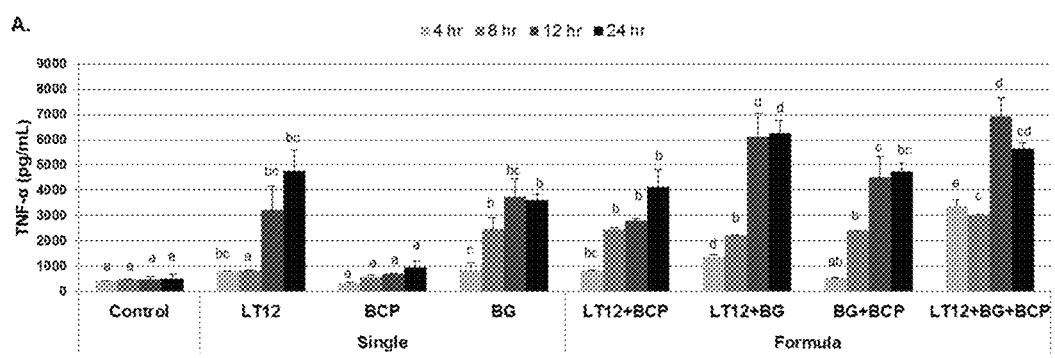
FIGS. 3A-3D show the effects of single ingredients and compound formulae of the samples on the secretion of various cytokines by macrophage RAW 264.7.

As shown in FIG. 3A, within 24 hours, the longer the stimulation time, the higher the TNF-α content induced. Compared with the non-stimulation group (Control), the highest folds of TNF-α content induced by each single ingredient were the 9.59-fold increase after 24 hours of LT12 stimulation, the 1.93-fold increase after 24 hours of BCP stimulation, and the 7.96-fold increase after 12 hours of BG stimulation, respectively. There was no increase in induction amount of TNF-α after 24 hours of BG stimulation, and it is inferred that the best action time of BG at this concentration is 12 hours. When compared the induction at the 12-hour time point, BG has the best ability to induce TNF-α secretion, followed by LT12, and BCP has relatively weak ability of induction. The groups of compound combinations containing BG had the highest induction amount of TNF-α at 12 hours. When compared the induction at the 12-hour time point, the compound combination containing all the three ingredients had the highest induction amount (14.81 folds) and had a synergistic effect.

Figure 3B:
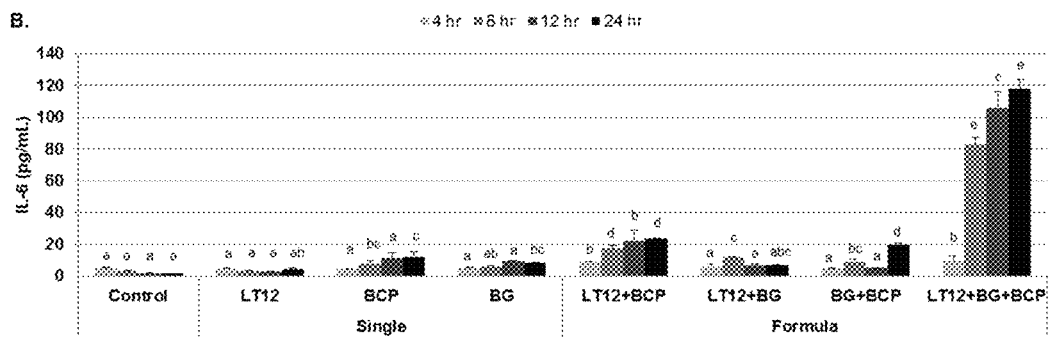

IL-6 has a similar trend to TNF-α, as shown in FIG. 3B, and the induction amount of both cytokines increased as the stimulation time increased. Compared with the non-stimulation group (Control), the highest folds of IL-6 content induced by each single ingredient were the 2.70-fold increase after 24 hours of LT12 stimulation, the 7.53-fold increase after 24 hours of BCP stimulation, and the 5.56-fold increase after 12 hours of BG stimulation, respectively. There was no increase in induction amount of IL-6 after 24 hours of BG stimulation, and it is inferred that the best action time of BG at this concentration is 12 hours. When compared the induction at the 24-hour time point, BCP has the best ability to induce IL-6 secretion, followed by BG, and LT12 has relatively weak ability of induction. The groups of compound combinations, except the group of LT12+BG, had the highest induction amount of IL-6 at 24 hours. Compared with other group, the compound combination containing all the three ingredients induced a 26.76-fold increase of IL-6 secretion after 8 hours of stimulation, and had the highest induction amount (72.92 folds) after 24 hours of stimulation, showing a significantly synergistic effect.

Figure 3C:
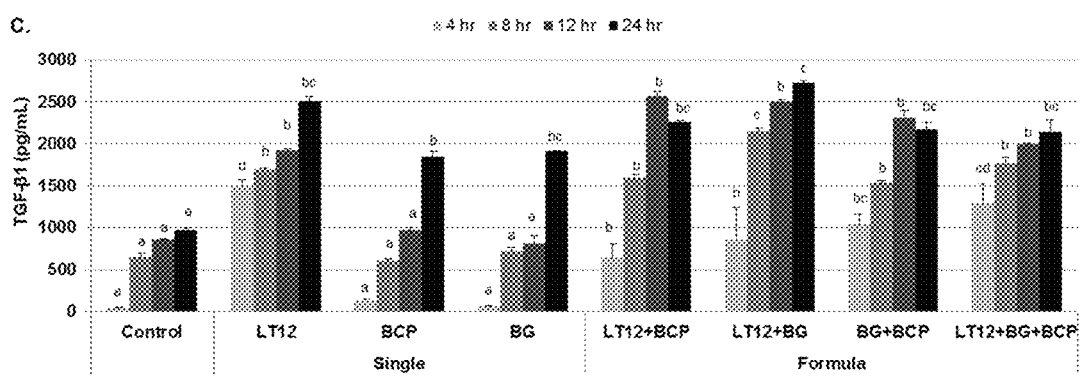

The result in FIG. 3C shows that although TGF-β1 secretion also increased as the stimulation time increased, compared with the non-stimulation group (Control), the highest induction fold of TGF-β1 secretion was reached in a short period of time (4 hours). Compared with the non-stimulation group (Control), the highest folds of TGF-β1 content induced by each single ingredient were the 35.26-fold increase after 4 hours of LT12 stimulation, the 3.25-fold increase after 4 hours of BCP stimulation, and the 1.97-fold increase after 24 hours of BG stimulation, respectively. When compared the induction at the 24-hour time point, LT12 has the best ability to induce TGF-β1 secretion, followed by BCP, and BG has relatively weak ability of induction. Specifically, the secretion amount of TGF-β1 induced by the single ingredient LT12 is much higher than other single ingredients. The highest induction fold of TGF-β1 secretion induced by the compound combinations also reached at 4 hours. Compared with other compound combinations, the compound combination containing all the three ingredients induced the most TGF-β1 secretion (30.51 folds), showing a synergistic effect.

Figure 3D:
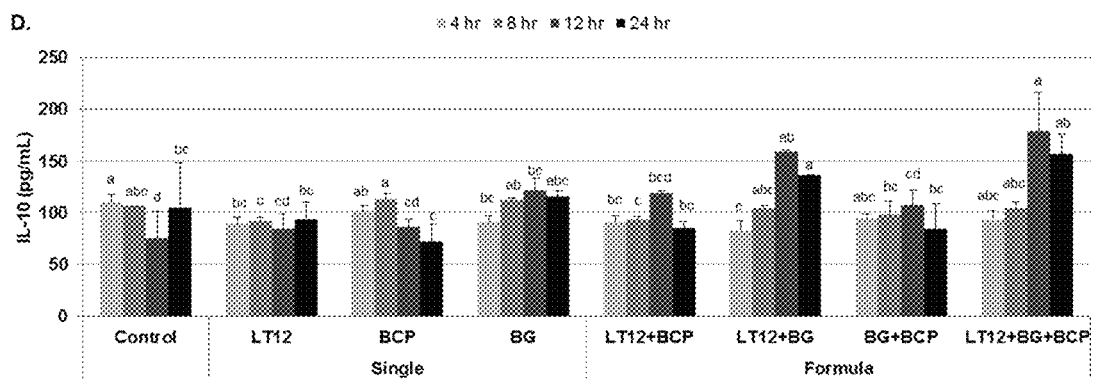

In terms of IL-10, FIG. 3D shows that compared with the non-stimulation group (Control), the content of IL-10 did not significantly increase as the stimulation time increased. Compared with the non-stimulation group (Control), the highest folds of IL-10 content induced by each single ingredient were the 1.11-fold increase after 12 hours of LT12 stimulation, the 1.13-fold increase after 12 hours of BCP stimulation, and the 1.61-fold increase after 12 hours of BG stimulation, respectively. The highest induction fold of IL-10 secretion induced by the compound combinations was reached at 12 hours. Compared with other compound combinations, the compound combination containing all the three ingredients induced the most IL-10 secretion (2.36 folds). Generally speaking, each single ingredient and their combinations at a certain concentration do not significantly increase IL-10 secretion in RAW264.7.

In conclusion, the present invention relates to a formula for a dietary supplement designed for immunomodulation based on the three main ingredients of the formula, LT12, BCP, and BG. It was unexpectedly found in the present invention that the combination of the three ingredients can efficiently induce the production of TNF-α, IL-6, and TGF-β1, indicating the immunomodulatory effects of the formula. All the three ingredients are essential to the best immunomodulatory effect, suggesting the synergistic or additive effects among the three ingredients. In general, the designed formula of the present invention has the potential for improving immunomodulation, and is suitable for daily and long-term consumption to achieve the effect of prevention and protection from pathogen infection.

We claim:

1. A composition for modulating immunity and with anti-allergic activities, comprising 0.5%-20% *Lactobacillus paracasei* LT12 (LT12), 0.5%-25% β-glucan (BG), and 0.05%-10% Bovine Colostrum Powder (BCP),
   as active components, in a percentage by total weight of the composition,
   wherein the expression of IL-6 is greater than the sum of the amount of IL-6 induced by a first composition comprising any two of LT12, BG and BCP and the amount of IL-6 induced by a second composition comprising the remaining one of LT12, BG and BCP.

2. The composition of claim 1, wherein the composition is effective in enhancing expression of tumor necrosis factor alpha (TNF-α), interleukin-10 (IL-10) and transforming growth factor-β1 (TGF-β1).

3. The composition of claim 1, wherein the composition comprises 1%-10% of LT12, 1%-12% of BG, and 0.05%-5% of BCP as active com ponents, in a percentage by total weight of the composition.

4. The composition of claim 3, wherein the composition comprises 1%-5% of LT12, 1%-6% of BG, and 1%-4% of BCP as active components, in a percentage by total weight of the composition.

5. The composition of claim 4, wherein the composition comprises
   2%-4% of LT12,
   4%-5% of BG and
   1%-2% of BCP
   as active components, in a percentage by total weight of the composition.

6. The composition of claim 1, wherein the composition does not affect viability of macrophage.

7. The composition of claim 1, wherein the β-glucan is β-1,3/1,6-glucan.

8. The composition of claim 1, which is a pharmaceutical composition for modulating immunity and with anti-allergic activities and further comprises a pharmaceutically acceptable carrier.

9. The composition of claim 1, which is a dietary supplement for modulating immunity and with anti-allergic activities and further comprises a dietary acceptable carrier.

10. A method for modulating immunity, comprising administering to a subject in need thereof a therapeutically effective amount of the composition as set forth in claim 1.

11. A method for modulating immunity, comprising administering to a subject in need thereof a therapeutically effective amount of the composition as set forth in claim 2.

12. A method for modulating immunity, comprising administering to a subject in need thereof a therapeutically effective amount of the composition as set forth in claim 3.

13. A method for modulating immunity, comprising administering to a subject in need thereof a therapeutically effective amount of the composition as set forth in claim 4.

14. A method for modulating immunity, comprising administering to a subject in need thereof a therapeutically effective amount of the composition as set forth in claim 5.

* * * * *